(12) United States Patent
Shakesheff et al.

(10) Patent No.: US 7,785,617 B2
(45) Date of Patent: Aug. 31, 2010

(54) POROUS MATRIX COMPRISING CROSS-LINKED PARTICLES

(75) Inventors: Kevin Morris Shakesheff, Nottingham (GB); Aliasger Karimjee Salem, Iowa City, IA (US)

(73) Assignee: The University of Nottingham, Nottingham (GB)

( * ) Notice: Subject to any disclaimer, the term of this patent is extended or adjusted under 35 U.S.C. 154(b) by 1125 days.

(21) Appl. No.: 10/481,923

(22) PCT Filed: Jun. 21, 2002

(86) PCT No.: PCT/GB02/02813

§ 371 (c)(1),
(2), (4) Date: Jul. 20, 2004

(87) PCT Pub. No.: WO03/000234

PCT Pub. Date: Jan. 3, 2003

(65) Prior Publication Data

US 2004/0241203 A1 Dec. 2, 2004

(30) Foreign Application Priority Data

Jun. 22, 2001 (GB) .................................. 0115320.4

(51) Int. Cl.
*A61F 2/00* (2006.01)
*C07K 14/00* (2006.01)
*A61K 38/00* (2006.01)

(52) U.S. Cl. .......................... 424/426; 514/2; 530/300; 530/350

(58) Field of Classification Search .................... None
See application file for complete search history.

(56) References Cited

U.S. PATENT DOCUMENTS

| | | | |
|---|---|---|---|
| 4,610,666 A | | 9/1986 | Pizzino |
| 4,728,570 A | * | 3/1988 | Ashman et al. ............. 428/327 |
| 4,861,714 A | * | 8/1989 | Dean et al. ................. 435/69.1 |
| 4,879,340 A | * | 11/1989 | Moriguchi et al. ......... 525/54.2 |
| 5,124,188 A | * | 6/1992 | Roe et al. ..................... 428/72 |
| 5,645,591 A | | 7/1997 | Kuberasampath et al. |
| 5,690,954 A | * | 11/1997 | Illum .......................... 424/434 |
| 5,714,589 A | | 2/1998 | Oppermann et al. |
| 6,387,124 B1 | * | 5/2002 | Buscemi et al. ............ 623/1.42 |

FOREIGN PATENT DOCUMENTS

| | | |
|---|---|---|
| JP | 3-504736 T | 10/1991 |
| WO | WO-90/10018 A1 | 9/1990 |
| WO | WO-91/18558 A1 | 12/1991 |
| WO | WO-99/11196 A1 | 3/1999 |
| WO | WO-00/01578 A1 | 1/2000 |
| WO | WO-01/35932 A2 | 5/2001 |
| WO | WO-02/07707 A2 | 1/2002 |

OTHER PUBLICATIONS

Stedman's Medical Dictionary 27th edition definition for cross-link.*
International Search Report for the Application No. PCT/GB02/02813, mailed Nov. 20, 2002.
International Preliminary Examination Report for the Application No. PCT/GB02/02813, completed Oct. 16, 2003.
Examiner's First Report on the corresponding Australian Patent Application No. 2002314317, from Australian Government: IP Australia, dated Feb. 14, 2008.
Lavelle, E.C. et al, "The stability and immunogenicity of a protein antigen encapsulated in biodegradable microparticles based on blends of lactide polymers and polyethylene glycol", Vaccine, 1999, vol. 17, pp. 512-529.
Notice of Reasons for Rejection for the Application No. 2003-506881 from Japan Patent Office mailed Mar. 10, 2009.
Black, Fiona et al., "Surface Engineering and Surface Analysis of a Biodegradable Polymer with Biotinylated End Groups", Langmuir, 1999, vol. 15, No. 9, pp. 3157-3161.
Canadian Office Action for the Application No. 2,456,286 from Canadian Intellectual Property Office dated Apr. 7, 2010.

* cited by examiner

*Primary Examiner*—Anand U Desai
(74) *Attorney, Agent, or Firm*—Cheng Law Group, PLLC (57) ABSTRACT

An open porous matrix of particulate material for in vivo use in or on a target tissue in medicine, the matrix comprising particles cross-linked with one another so as to define pores there between and uses therefor are described.

13 Claims, 5 Drawing Sheets

POROUS MATRIX COMPRISING CROSS-LINKED PARTICLES

This invention relates to matrices of particulate material. More particularly, the present invention relates to, matrices of particulate material which are usable in medicine, including veterinary medicine.

Matrices of particulate material are known to be used in medicine for use as tissue scaffolds, however, the matrix of the present invention is usable both as a tissue scaffold and as a delivery system for drugs or other therapeutic agents.

Many patent applications describe the use of gels or sols, especially hydrogels for use as tissue scaffolds. For example, WO 00/23054 describes the use of polyvinyl alcohol microspheres in the occlusion of blood vessels or embolizations. WO 99/15211 and WO 00/64977 describe the use of hydrogels as a tissue scaffold. The hydrogels are implanted into a patient in order to support tissue growth and/or repair.

The use of hydrogels as tissue scaffolding is problematical in that although the gels themselves may adequately fill the cavity in to which they are inserted, they have poor diffusion properties and as such drugs, nutrients or other factors to be supplied to the gel do not adequately diffuse through the gel. This problem is exacerbated where the gel is seeded with living cells since the poor diffusion of nutrients can lead to premature cell death possibly resulting in failure of the treatment. A further problem associated with gel scaffolds is that the cross-linking methods used to stabilise or solidify the gels, especially in situ, can damage the entrapped cells.

Scaffolds based on water-insoluble polymers are also known in the art, for example WO 99/25391 describes the use of poly (lactide-co-glycolide) (PLGA) as a polymer scaffold for the regeneration of tissue, especially bone tissue. The polymers are processed so as to form a porous structure. As with the hydrogels, the water-insoluble polymers are implanted into a patient in order to support tissue growth and/or repair.

However, the disadvantage of such water-insoluble polymers is that they can only fill cavities with an open shape and methods of shaping the materials are yet to be perfected. Additionally, where the scaffold is to be seeded with cells, the seeding is inefficient (few pores are filled with cells) or the cells are damaged by the structure during the seeding process, and the surrounding tissue cells may also be damaged by the implantation procedures.

WO 99/11196 describes the use of a particulate matrix as tissue scaffold, the particles having internal cross-linking to stabilise the structure of the particle. In WO 99/11196 the cross-linking described is within the particle hence it is able to stabilise the particle. However, there is no cross-linking between particles, i.e. particle-particle cross-linking to stabilise the matrix per se is not described. Hence, the cross-linking described in WO 99/11196 is intra-particle not inter-particle.

It is therefore an object of the present invention to provide a matrix which overcomes the problems associated with known matrices, that is, one which allows diffusion of material through the matrix, can conform to the desired shape without damaging any cells which may be seeded therein and which does not damage any cells which are being seeded therein.

Accordingly, the present invention provides an open porous matrix of particulate material for use in or on a target tissue in medicine, including veterinary medicine, the matrix comprising particles cross-linked with one another so as to define pores therebetween.

The advantage of the matrix of the present invention is that the pore structure is well defined by virtue of the cross-linking between the particles rendering the matrix stable. That is, each particle is cross-linked to one or more other particles in the matrix.

The presence of the pores allows the matrix to be seeded with cells for use in tissue regeneration, or to enable diffusion of drugs, nutrients or other therapeutic agents through the matrix. Alternatively, the matrix or each particle therein may be surface engineered to attract and/or to retain cells or peptide fragments so as to form extra-cellular matrix for tissue regeneration. For example, the matrix may have associated peptide fragments retained thereon to attract and retain cells on or within the matrix.

The present invention also provides a fluid composition comprising particulate material, and a cross-linking agent, the particles cross-linking to form a matrix on introduction to the cross-linking agent in or on a target tissue.

Advantageously, the particles, and any other agent to be delivered to the patient, and the cross-linking agent are mixed before or during administration to the patient and the matrix is formed in situ thereby conforming to the shape of the target or delivery site. Preferably, the particles, and the cross-linking agent are administered to the patient simultaneously, ideally they are co-delivered to the target or delivery site.

The particles, and the cross-linking agent may be administered by parenteral, topical or oral delivery. Preferably, the particles are delivered by co-injection to an internal target site and topically to an external site.

An advantage of co-injection delivery to an internal target site is that the introduction of the matrix to the target site is minimally invasive to the patient being treated.

The matrix may be used as a scaffold for the growth of new tissue or it may be used as a delivery system or implant for pharmaceuticals, vaccines, hormones (including contraceptive hormones), enzymes, nutrients or other therapeutic agents or factors. The particles used are generally within the range of 1 nm to 1 mm, and preferably in the range of from 100 nm to 500 µm depending on use. Preferably, particles in the nanometer range are used as delivery system or implant while particles in the micrometer range are used as a tissue scaffold. However, it is not intended that the invention be limited to these size/use preferences as some applications of an implant may require micrometer sized particles, for example an inter-uterine implant for contraceptive or tumour treatment, and some applications as a tissue scaffold may require nanometer particles, for example within the spinal column or the brain.

The particles are preferably hard or solid particles although mixtures of solid and semi-solid or soft particles are not to be excluded from the scope of the present invention. Soft particles such as liposomes may be usable in the present invention but current liposome technology does not allow the production of a sufficiently robust particle to give the strength needed for the envisaged uses of the invention. However, a mixture of hard particles and liposomes may be used, the liposomes preferably dispersing through the matrix to release the substances, for example antibiotics, therein to the surrounding tissue and through the matrix.

For example, the particles may be made from natural or synthetic polymers such as silk, elastin, chitin, chitosan, poly (αhydroxyacids) especially polylactic or polyglycolic acids, poly (anhydrides) or poly(ortho esters). Polymers of polyhydroxy acids including polyhydroxybutyric acid, lactic, glycolic and s-caproic acid, polyanhydrides, polyorthoesters, polyphosphazenes, polyphosphates, polycaprolactone or copolymers prepared from the monomers of these polymers can be used (see for example the methods described in WO 95/03357).

The particles may be at least partially hollow or adsorbent to allow the particle to uptake a substance to be released at the target site. For example, where sustained slow delivery of a substance to the target site is desired the particle may encapsulate, be filled with or be impregnated with a substance which will either slowly be released by diffusion or will be released as the particle is broken down by the body's natural metabolic processes. The ability to be able to protect substances from the action of the body and thereby delay or sustain their release is advantageous, for example where a slow release of a growth promoter or a tumour inhibitor is required, or, for example, in the case of delayed release, where a core of a substance representing a "stop" signal, such as a morphogenetic protein, is embedded within a particle for release only after a predetermined degradation period.

Preferably, the particles are co-formed with the substance to be released at the target site. In the most preferred embodiment a multi-lamellar technique is used so that a bolus or boli of substance become embedded within the particle.

Alternatively, the particles may be coated in a substance intended for immediate or very short term release, for example, an antibiotic to prevent infection of the target site or an integrin target or other target ligand for cell receptors to promote adhesion of the surrounding cells to the matrix. It is especially preferred that at least the outer portion of the matrix is so coated.

Examples of substances which can be in or on the particle include epidermal growth factor (EGF), nerve growth factor, insulin-like growth factor (IGF), basic fibroblast growth factor (bFGF), platelet derived growth factor (PDGF), transforming growth factor-P and related growth factors, for example bone morphogenetic proteins (BMPs), cytokines including interferons, interieukins, monocyte chemotactic protein-1 (MCP-1), oestrogen, testosterone, kinases, chemokinases, glucose or other sugars, amino acids, dopamine, amine-rich oligopeptides, such as heparin binding domains found in adhesion proteins such as fibronectin and laminin, other amines tamoxifen, cis-platin, peptides and certain toxoids. This list is intended as illustrative and is not intended to be limiting in any way. As described above, any substance such as a drug, hormone, enzyme, nutrient, or other therapeutic agent or factor or mixtures thereof may be in or on the particle.

The particles may be formed from biodegradable material. The term "biodegradable material" as used herein is intended to mean that the material dissolves or is broken down or fragmented within a period that is acceptable in the desired application and is less than or about five years, preferably between one hour and five years, more preferably between one day and one year, and ideally between one week and one year.

Conveniently, the rate of dissolution or degradation is measured on exposure to a physiological saline solution of between pH 6.0 and 8.0 at a temperature of between 25° and 37° C., for example, pH 7.0 at 30° C., although other methods may be used. It will be appreciated that the size and shape of the sample may have some influence on the degradation rate and that tests may preferably be carried out with samples of a similar shape and size to those intended to be used in practice. The influence of size and shape is significant for biodegradable materials that undergo surface erosion. These materials erode (degrade) from the surface only and therefore the surface area of any particle will determine the rate of removal of biomaterial. Surface eroding polymers include those of the polyanhydride and poly (ortho ester) classes. Most other biodegradable polymers are bulk eroding (i.e. degradation occurs throughout the polymer article, not just at the surface), including the lactic acid and glycolic acid based polyesters.

Preferably, the particles are made from a material which is biocompatible. The term "biocompatible" as used herein is intended to define a material and its degradation products which are not unacceptably immunogenic, allergenic or toxic. Ideally, the particles are both biodegradable and biocompatible.

Suitable synthetic biodegradable polymers are set out in list form below:
1. Polyesters including:
   poly(lactic acid)
   poly(glycolic acid)
   copolymers of lactic and glycolic acid
   copolymers of lactic and glycolic acid with poly(ethylene glycol)
   poly (E-caprolactone)
   poly (3-hydroxybutyrate)
   poly (p-dioxanone)
   poly (propylene fumarate)
2. Poly (ortho esters) including:
   Polyol/diketene acetals addition polymers (as described by Heller ACS Symposium Series 567,292-305, 1994).
3. Polyanhydrides including:
   poly (sebacic anhydride) (PSA)
   poly (carboxybiscarboxyphenoxyphenoxyhexane) (PCPP)
   poly [bis (p-carboxyphenoxy) methane](PCPM)
   copolymers of SA, CPP and CPM 9 as described by Tamada and Langer in Journal of Biomaterials Science Polymer Edition, 3,315-353,1992 and by Domb in Chapter 8 of the Handbook of Biodegradable Polymers, ed. Domb A. J. and Wiseman R. M., Harwood Academic Publishers).
4. Poly (amino acids)
5. Poly (pseudo amino acids) (including those described by James and Kohn at pages 389-403 of Controlled Drug Delivery Challenges and Strategies, American Chemical Society, Washington D.C.).
6. Polyphosphazenes including:
   derivatives of poly [(dichloro) phosphazene]
   poly [(organo) phosphazenes]
   polymers described by Schacht in Biotechnology and Bioengineering, 52,102-108,1996.

In a preferred embodiment polyesters of poly (lactic-co-glycolic) acid (PLGA) are used. These polymers are approved for parenteral administration by the FDA. Because PLGA degrades via non-enzymatic hydrolysis in the initial stages, in vivo degradation rates can be predicted from in vitro data. PLGA degrades to lactic and glycolic acids, substances found naturally in the body.

Copolymers with amino acids may be synthesised, for example glycolic acid and glycine, or lactic acid and lysine (Barrera et al (1993) J Am Chem Soc 115,11010-11011 and Cook et al (1997) J Biomed Mat Res 35, 513-523). These may be useful for immobilising other molecules, for example via the lysyl s-amino moieties. These polymers may be used to attach peptides to surfaces using covalent bonds. For example, peptides may be attached to poly (lactic acid-co-lysine) using 1,1'-carbonyl-diimidazole (CDI, Aldrich) as a linking agent as described in the above references.

By manipulating the molar ratio of lactic and glycolic acid and the molecular weight of the copolymers, different degradation patterns can be obtained. Poly-L-lactide has a degradation time in vitro of months to years. The long degradation time is due to its high crystallinity which protects the polymer from water penetration. Poly-glycolide has a degradation time of one to several months, whereas poly-D, L-lactide is amorphous and has a degradation time of one to a few months. D, L PLGA has a degradation time in vitro of weeks to months. As the glycolic acid ratio is increased, the rate of degradation increases. Homopolymers of s-caproic acid can remain intact for 2-3 year periods of implantation.

It will be appreciated that the degradation time of a polymer may be altered when other molecules are incorporated.

PLA-PEG-biotin is a biocompatible, biodegradable solid polymer with amphiphilic properties that generate a hydrophilic surface region that is particularly preferred in embodiments of the invention.

Copolymers with polyalkylene glycol, for example PEG, reduce the level of inflammation seen. Copolymers comprising a polyalkylene glycol are preferred to those without polyalkylene glycol. The polyalkylene glycol also helps to reduce non-specific protein absorption. To ensure elimination from the body, the PEG should have a molecular weight of between approximately 300 and 20,000 Daltons. The rate of hydrolysis is also increased for copolymers containing a biodegradable component with polyalkylene glycols.

Other surfactants are usable in the present invention, however some surfactants coat the particle in a manner such that the cross-linking agent cannot sufficiently attach to the particle. For example, where biotin is used as a cross-linking agent, use of PVA on PLA as a surfactant would prevent the biotin from bonding onto the particle surface and hence no cross-linking would occur.

In this manner compatible cross-linking agents and surfactants should be chosen.

In one of the presently preferred embodiments, PEG is used and the PEG is generally found within the particle rather than as a coating and as such minimizes the possibility of adversely coating the particle, preventing bonding by the cross-linking agent.

Advantageously, the PEG also stabilises the surface of the particle during manufacture.

The cross-linking agent may be any known cross-linking agent which is non-cytotoxic or non-cytostatic. One of the preferred cross-linking agents is a biologically active ligand. Ideally, the cross-linking agent is of the "anchor-adapter-tag" system type (as described in patent application no PCT/GB99/001921, the content of which is incorporated herein by reference), in which an adapter which can interact specifically and with high selectivity with an anchor molecule present on a particle, and a tag molecule present on a further particle.

It will be appreciated that the said specific molecular interaction required in this aspect of the invention may occur between a component of the particle surface and the biologically active ligand molecule (which may, for example, be a fusion molecule, for example with a biologically active domain and a domain that interacts with the said component of the particle surface). Alternatively, for example, it may occur between a component of the particle surface and an adapter molecule, as described above, and/or between the said adapter molecule and the biologically active ligand molecule or a tag attached thereto.

It will also be appreciated that it is necessary only that a biologically active ligand molecule is attached to the said particle surface by means of one specific molecular interaction; any other molecular interactions involved need not be specific molecular interactions. However, it should be understood that it may be preferable if more than one molecular interaction is involved per ligand molecule, then more than one of the said molecular interactions may be a specific molecular interaction. Thus, the interaction between the particle surface and an adapter, and between the said adapter and a tag, may, but do not have to, both be specific molecular interactions. The adapter may comprise more than one component, such that a chain of components links the ligand to the particle surface; each interaction may, but does not have to, be a specific molecular interaction.

It will be appreciated that an adapter molecule, for example, may be able to form specific molecular interactions with more than one molecule, or more than one type of molecule. For example, the adapter may have a specific molecular interaction with an anchor molecule and a further specific molecular interaction with a tag molecule; the anchor and tag molecule may be the same chemical entity, for example biotin, or may be different.

The cross-link is preferably of the anchor-adaptor-tag type as hereinbefore described. The links between the particle and the cross-linker may be of any type but strong bonding is to be preferred. The bond may form spontaneously after the specific molecular interaction has taken place, or it may require catalysis. It will be appreciated that such a bond may form between the molecules that participate in a specific molecular interaction, for example between an anchor molecule and an adapter molecule, or between other molecules, for example between the biologically active ligand and a molecule present on the said particle surface that does not form a specific molecular interaction with the ligand. It is preferred that the bond is a covalent bond, or at least has a bond strength in the order of covalent bond strength or bond energy. However, ionic, electrostatic or hydrogen bonds may be used with equal utility according to the nature of the molecules being bonded or the nature of the application or the target tissue.

In a particularly preferred embodiment, the anchor and the tag are biotin and the adapter is avidin or streptavidin. The valency of biotin is one, and that of streptavidin or avidin is 4. The Kd for the binding of biotin to streptavidin/avidin is about $10^{-15}$M. This binding is far stronger than many non-covalent interactions, for example antibody/antigen interactions. This system therefore provides an extremely high affinity and long lasting binding.

In the most preferred embodiment both the anchor and the tag are biotin and the adapter is avidin. This system is preferred since both biotin and avidin are cell compatible linkers and since the bonds between the avidin and the biotin are non-covalent yet are stronger than other interactions of the molecular recognition type.

Advantageously, the tetrameric binding sites of the avidin allow the biotin to carry another substance to be delivered to the target site, within the matrix. For example biotinylated proteins or sugars and the like.

Conveniently, the matrix may also cross-link with the surrounding tissue. Optionally, with the use of the same cross-linking reaction and agent.

Other cross-linking strategies include the use of charged particles or polymers, acrylate cross-linking, and the surface coating of particles with biopolymers.

For example, charged polymers may be used to adsorb, absorb, trap, entrap, bind or adhere the microparticles to one another by use of electrostatic interactions. Polymers such as poly(aspartic) acid and poly(lysine) may be used in this method.

Acrylate cross-linking may be used by synthesising PLA-PEG-Acrylate particles and cross-linking them to one another by the use of UV light in the presence of an initiator.

Particles may be cross-linked to one another by virtue of their surface coatings. For example, if the particles are coated with a gel or a sticky coating, such as alginate, agarose or fibrin it is possible to exploit the gel properties or stickiness to cross-link the particles to one another for example by creating adhesion via gelation using salt, temperature or a clotting factor, such as factor XIIIa, for alginate, agarose or fibrin, respectively.

Ideally, the cross-linking reaction occurs in the presence of a spacer compound. The spacer compound may be any hydrophilic spacer compound such as dextran or polyalkylglycols such as Polyethylene Glycol (PEG). The concentration of the spacer compound required is variable according to the desired pore size of the matrix.

The pore size is generally selected according to the function of the matrix. The pore size can be controlled by the particle size and shape, by the concentration of particles and by the nature of the cross-linking, for example by varying the number of adapters used in the anchor-adaptor-tag type linkage.

In a second embodiment of the present invention the matrix is seeded with cells and the matrix is used as a scaffold for tissue regeneration.

In this embodiment the pore size is ideally of between 1 and 25 times the cell diameter to enable sufficient seeding of viable cells. The pore size may be reduced from 25 times the cell diameter to suit the application. Advantageously, the formation of the matrix in situ reduces the amount of damage to the cells during the seeding process since the cells are not physically inserted into the matrix, as in the prior art, rather the matrix is formed about the cells. In this manner, more of the cells used to seed the matrix remain viable for tissue regeneration.

At present it is understood that the matrix of the present invention can be used in any tissue, living, necrotising or dead, including bone and cartilaginous tissue. Examples of tissues where the seeded matrix can be used are spinal disc regeneration, autologous chondrocyte implantation, spinal cord repair, cell delivery to the brain, especially for the use in the treatment of Alzheimer's and Parkinson's diseases, liver regeneration, osteoarthritis, bone cavity filling, soft tissue augmentation for example in urology or breast augmentation optionally following mastectomy, implantation of in vitro fertilized embryo, regeneration of the pancreas in diabetes mellitus, or the regeneration or repair of tissues which require vascularization or angiogenesis.

The matrix may be seeded with any type of cell, but especially preferred are donor cell chondracytes, stem cells from another part of the body or from embryos, and reprogrammed cells from other parts of the body such as adipocytes reprogrammed to become cartilage cells.

In use as a matrix for the delivery of a drug or the like, it is preferred that a suspension of particles is formed, optionally with the spacer agent, and a separate solution of avidin is prepared. The suspension and the avidin are co-applied to the area to be treated, and the matrix forms and hardens in situ. Where the suspension and the solution are to be co-injected, they are preferably introduced to one another in the target area. However, it may be that the two are introduced to one another in the needle from a double barrelled syringe.

Where the matrix is to be seeded with cells, the cells and the particles, and the optional spacer agent are mixed together in a single suspension to be introduced to the avidin. The cell suspension is introduced to the avidin in the manner described above.

In another aspect of the invention a method of forming a matrix of open porous particulate material for use in medicine, including veterinary medicine, is provided, the method comprising the steps of forming a suspension of particulate material, separately forming a solution of a cross-linking agent and introducing the particle suspension to the cross-linking solution in situ in or on a target tissue.

Alternatively, the matrix may be formed from a suspension of particles with the cross-linking agent, and a separate suspension of particles the two suspensions being introduced to one another in situ in or on a target tissue.

Hence the present invention further provides a method of forming a matrix of open porous particulate material for use in medicine, including veterinary medicine, the method comprising the steps of forming a suspension of particulate material and a cross-linking agent, forming a separate suspension of particles and introducing the suspended particle and cross-linking agent to the suspended particles in situ in or on a target tissue.

Where the matrix is intended to be seeded with cells, the cells may be added to either or both suspensions. Preferably, however, the cells are not added to the suspension containing only avidin.

The particulate material and the cross-linking agent are as hereinbefore described.

The suspension and the solution may be introduced to one another sequentially or simultaneously, preferably sequential administration is in rapid succession. Ideally, the suspension and the solution are introduced simultaneously.

In a fourth aspect the invention provides methods of treatment of the human or animal body using the matrix of the present invention.

Accordingly, the present invention provides a method of treatment of an animal, the method including the introduction of an open porous matrix of particulate material formed from a co-administered suspension of particulate material and of a cross-linking agent introduced to one another in situ in or on a target tissue of an animal in need of treatment.

The matrix is preferably as hereinbefore described.

Diseases or other conditions treatable with the method of invention include, but are in no way limited to Alzheimer's disease, Parkinson's disease, osteoarthritis, burns, spinal disk atrophy, cancers, hepatic atrophy and other liver disorders, bone cavity filling, regeneration or repair of bone fractures, diabetes mellitus, ureter or bladder reconstruction, prolapse of the bladder of the uterus, IVF treatment, muscle wasting disorders, atrophy of the kidney, organ reconstruction and cosmetic surgery.

In a final aspect the invention provides apparatus for delivering the matrix to the target site, the apparatus comprising a syringe having a plurality of barrel chambers, each of which barrels dispenses into a common discharge aperture. Optionally a hypodermic needle is attached to the common discharge aperture. The syringe is preferably used in the method of the present invention to deliver the matrix of the present invention.

BRIEF DESCRIPTION OF THE DRAWINGS

Embodiments of the invention will now be described by way of example only with reference to the following drawing, of which.

EXAMPLE 1

Preparation of Microparticles

The polymer PLA-PEG-biotin was prepared as described in Cannizzaro, S. M., et al. A novel biotinylated degradable polymer for cell-interactive applications. Biotechnology and Bioengineering 1998;58:529-535. Then, microparticles were manufactured. Briefly, 500 mg of PLA-PEG-biotin was dissolved in 20 ml of dichloromthane (DCM) to produce a 25 mg/ml solution. PVA (250000 Mw) [88% hydrolysed] was dissolved into ELGA water (0.25 g into 250 ml) to make a 0.1% w/v solution. The PLA-PEG-biotin solution was then added to a homogenised PVA solution using a 5 ml Gilson pipette. The mixture was homogenised for a further 10 minutes at 5000 rpm and then left stirring overnight for DCM to evaporate and microparticles to form. Nanoparticles were prepared as above with a 9% PVA solution and homogentisation at 5000 rpm and a 5 mg/ml solution of PLA-PEG-biotin.

| PVA conc. (%, w/w) | Stirring Rate (rev./min) | Average Size (micron) |
|---|---|---|
| 0.1 | 1500 | 9.9 |
|  | 3500 | 5.2 |
|  | 5000 | 2.1 |
| 1 | 1500 | 3.2 |
|  | 3500 | 1.9 |
|  | 5000 | 1.7 |
| 9 | 1500 | 1.4 |
|  | 3500 | 0.6 |
|  | 5000 | 0.25 |

EXAMPLE 2

Cross-Linking of Microparticles with Avidin

Figure 1:
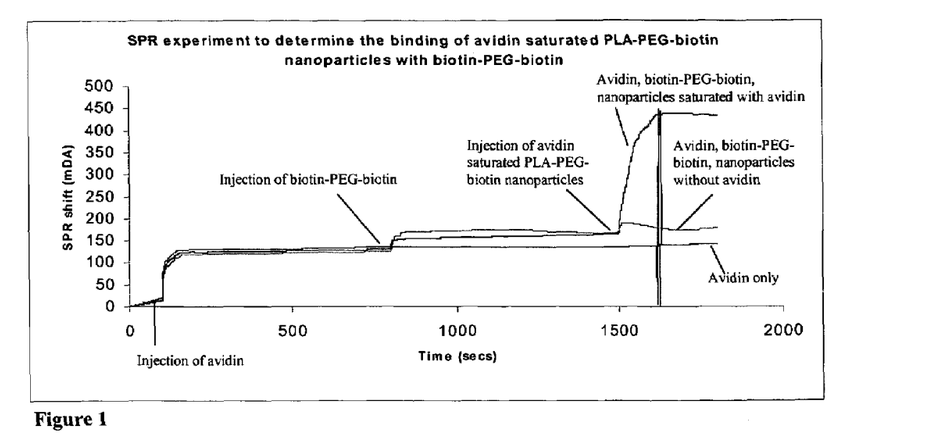
FIG. 1 shows a surface plasmon resonance experiment to determine the binding of avidin saturated PLA-PEG-biotin nanoparticles with biotin-PEG solution.

Surface plasmon resonance analysis was used to prove that microparticles could be cross-linked with avidin. (FIG. 1)

The SPR equipment (Ortho Clinical Diagnostics, Chalfont, St-Giles, UK) employs a Kretschmann configuration with a monochromatic laser source of 780 nm wavelength. The glass slides had a 50 nm silver layer on one side. These were biotinylated by incubating each slide in a 0.1 mg/ml solution of N-([6-biotinamido-]hexyl-)3'-[2'pyridylthio]propionamide in TFE. Sample solutions of avidin ($1.5 \times 10^{-7}$ M), biotin-PEG(3350)-biotin ($1 \times 10^{-6}$ M). PLA-PEG-biotin particles (250 nm) were saturated in excess avidin and washed using centrifugation. The avidin-saturated particles ($1.5 \times 10^{-7}$ M), were then prepared in 10 mM sodium phosphate buffer (pH 7.4). For the purposes of a stable baseline reading, a sodium phosphate buffer wash (10 mM, pH 7.4) was first passed over the biotin-HPDP functionalised surface for 100 s. Avidin functionalised surfaces were then obtained by flowing avidin solution ($1.5 \times 10^{-7}$ M) over the biotinylated slides. To remove any excess streptavidin, sodium phosphate buffer (10 mM, pH 7.4) was then washed over the surface. In the next stage of the experiment, the biotin-PEG(3350)-biotin ($1 \times 10^{-6}$ M) was flowed across the sample surface, followed by a buffer wash to remove unbound biotin-PEG(3350)-biotin. Avidin-saturated nanoparticles ($1.5 \times 10^{-7}$ M) were then flowed over the surface followed by a buffer wash. As a control experiment, unsaturated PLA-PEG-Biotin nanoparticles ($1.5 \times 10^{-7}$ M, 250 nm), were injected in place of the avidin-saturated nanoparticles following the avidin and biotin-PEG-biotin injections. A further control involved injecting avidin alone over the experimental time period. The flow rate was 0.24 mL/min with results taken from at least 8 repeats. The change in the SPR angle was monitored over time, in units of millidegrees angles (mDA) where 1 mDA=0.001°.

EXAMPLE 3

Aggregation of Microparticles

Aqueous suspensions of microparticles were added to solutions of avidin. Aggregation resulted in an increased size of particles and was recorded by light microscopy.

Figure 2:
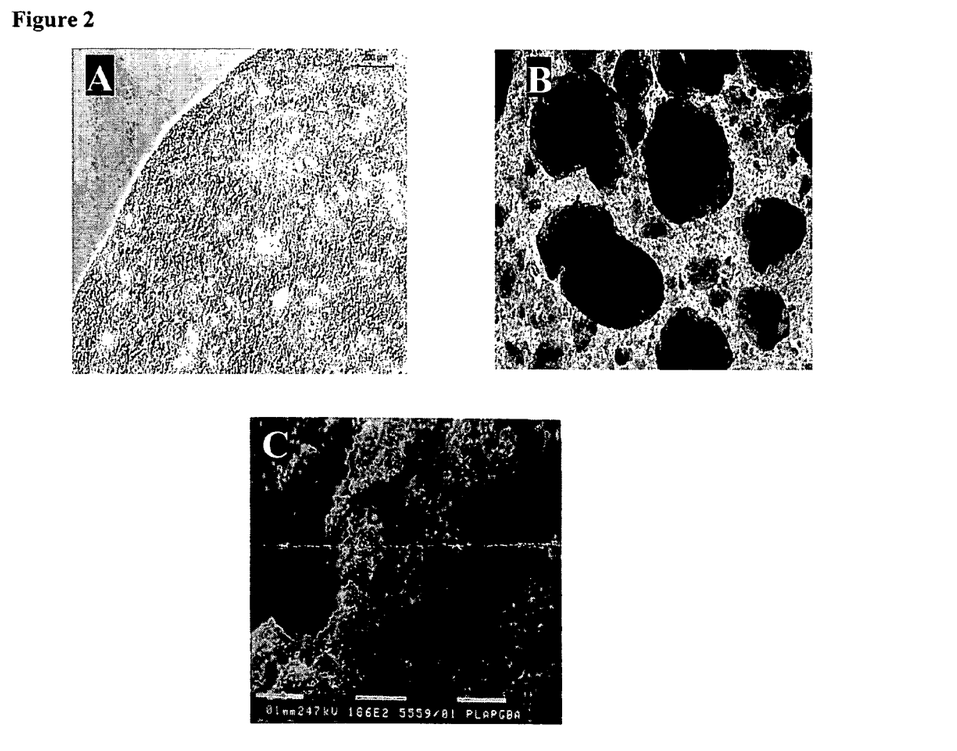
FIG. 2 shows PLA-PEG-biotin microparticles [A] without avidin & [B] with rhodamine conjugated avidin illustrating aggregation, [C] is an SEM image of an assembled scaffold illustrating porosity.

See FIG. 2 which shows a microscopy image of 10 micron PLA-PEG-biotin microparticles [A] without avidin and [B] with rhodamine conjugated avidin illustrating aggregation. [C] illustrates the porosity of an assembled scaffold.

EXAMPLE 4

Formation of 3D Structures

Figure 3:
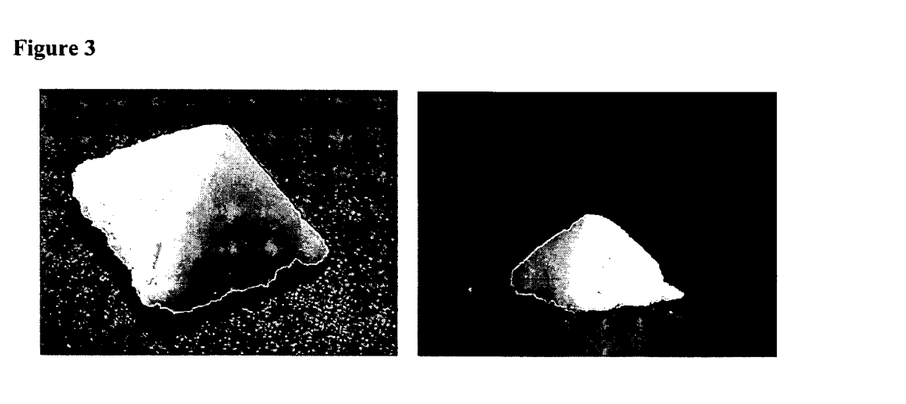
FIG. 3 shows a matrix formed in a pyramid shaped mould.

PLA-PEG-biotin microparticles and an aqueous solution of avidin was co-injected into a pyramid shaped mould. The resulting structure was a free standing scaffold. (FIG. 3)

EXAMPLE 5

Formation of Cell-Scaffold Composites

Cell Culture Experiments

HOS cells were cultured in Dulbecco's modified Eagle's Medium (DMEM) supplemented with 10% foetal calf serum (FCS), 2 mM L-glutamine, 100 U/ml penicillin, 100 g/ml streptomycin and 0.25 µg/ml amphotericin B (antibiotic/antimycotic). Cell cultures were incubated at 37° C. in a 5% $CO_2$ enriched atmosphere. Every 2 to 3 days the cells were removed from the tissue culture flasks, using 0.25% trypsin/1 mM EDTA in PBS, reseeded.

Cells were incubated with Cell Tracker™ green CMFDA (5-chloromethlyfluorescein diacetate) fluorescent stain (Molecular Probes), by reconstituting the material in 11 µl DMSO and adding this solution to the media of a confluent tissue culture flask for 45 min. The media were then replaced and the cells incubated for a further hour. Following trypsinisation and resuspension, the cells were centrifuged and resuspended in DMEM. Approximately 1 million cells were placed into a mixture of 50% avidin saturated PLA-PEG-biotin microparticles and 25% biotin-PEG-biotin was added to this to aggregate the microparticles and entrap the cells. Scaffolds were examined using a confocal microscope.

Figure 4:
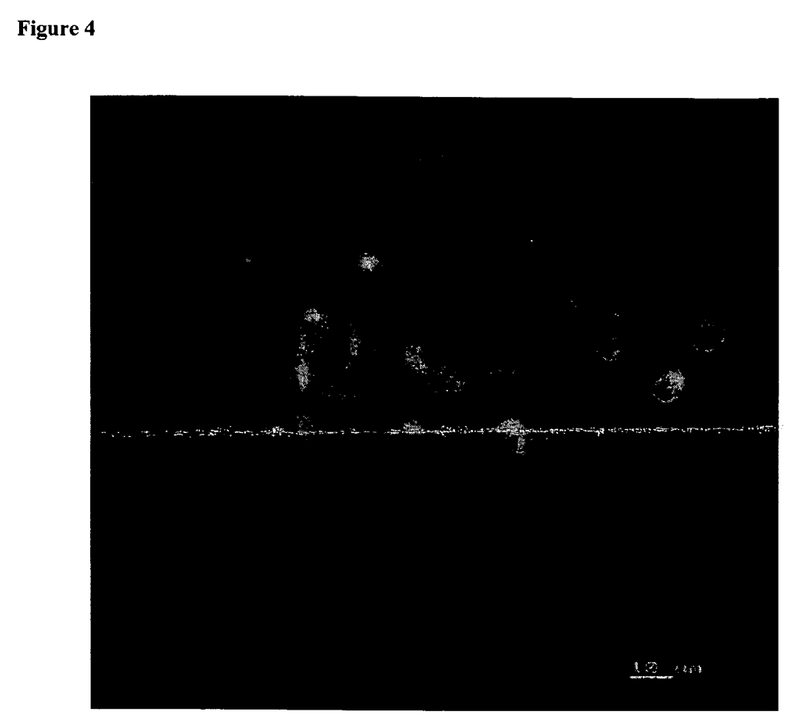
FIG. 4 shows a confocal image of entrapped HOS cells (containing cell tracker) within cross-linked scaffold.

See FIG. 4 which shows confocal image of entrapped HOS cells (containing cell tracker) within cross-linked scaffold (dark grey/black region shows the reflectance) (cells are shown in light grey).

EXAMPLE 6

Injection Formation of Polymer/Cell Composite Scaffolds

Agarose gels were prepared at 0.5% concentrations. Scaffolds using 25% Biotin-PEG-biotin, 50% avidin saturated PLA-PEG-biotin microparticles and $1 \times 10^6$ HOS cells were injected into the agarose gels. As a control, 25% Biotin-PEG-biotin, 50% PLA-PEG-biotin microparticles (without avidin) and $1 \times 10^6$ HOS cells were injected into the agarose gels. A further control was to inject a scaffold using 25% Biotin-PEG-biotin, 50% avidin saturated PLA-PEG-biotin microparticles with no cells.

Figure 5:
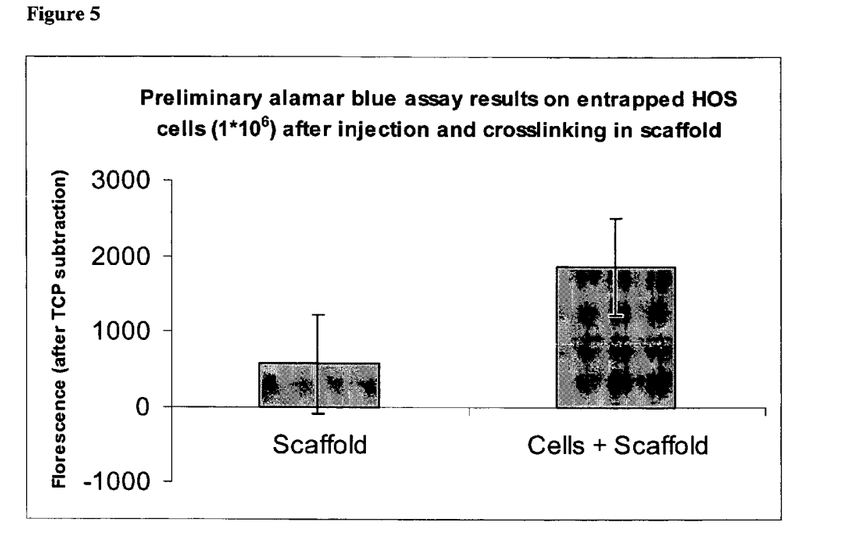
FIG. 5 is a graph showing uptake of Alamar blue by viable cells and by the matrix.

The Alamar blue assay was carried out using HOS cells entrapped within scaffold and this confirmed the viability of entrapped cells. Blanks using tissue culture plastic and scaffolds without cells were carried out as comparisons. 100 .mu.l samples were taken from each sample placed into a 96 well plate which was gently shaken for 5 minutes. Measurements were made using a plate reader at 530 excitation (Ex), 590 emission (Emm) with a sensitivity of 50. (See FIG. 5)

EXAMPLE 7

Chorioallantoic Membrane (CAM) Culture

Fertilised eggs were incubated for 10-18 days using a Multihatch automatic incubator (Brinsea Products, Sandford, UK) at 37° C. in a humidified atmosphere. On day 10, eggs were removed and a 1 cm² square section cut into the shell. Scaffolds were injected drop-wise directly onto the CAM of 10 day old chick embryos and incubation continued for a further 7 days. In addition, femurs were excised from day 18 chick embryos and a wedge-shaped segmental defect created in the middle of the femur, into which the scaffold was injected to fill the defect site. The femoral/scaffold explant was then placed onto the CAM and incubation, at 37° C., continued for a further 7 days as previously detailed[15]. Explants were then harvested and the chick embryo killed by decapitation. Prior to histochemical analysis, scaffold and explant samples were then fixed in 95% ethanol, processed to paraffin wax and 5 μm sections prepared. Sections were stained with Alcian blue/Sirius red and alkaline phosphatase to demonstrate proteoglycan, collagen and enzyme activity as follows:

i) Alkaline phosphatase activity: Samples were stained using a Sigma alkaline phosphatase kit (no.85).

ii) Alcian blue/Sirius red: Samples were stained using Weigert's haematoxylin, alcian blue (in 1% acetic acid) and sirius red (in saturated Picric acid).

Figure 6:
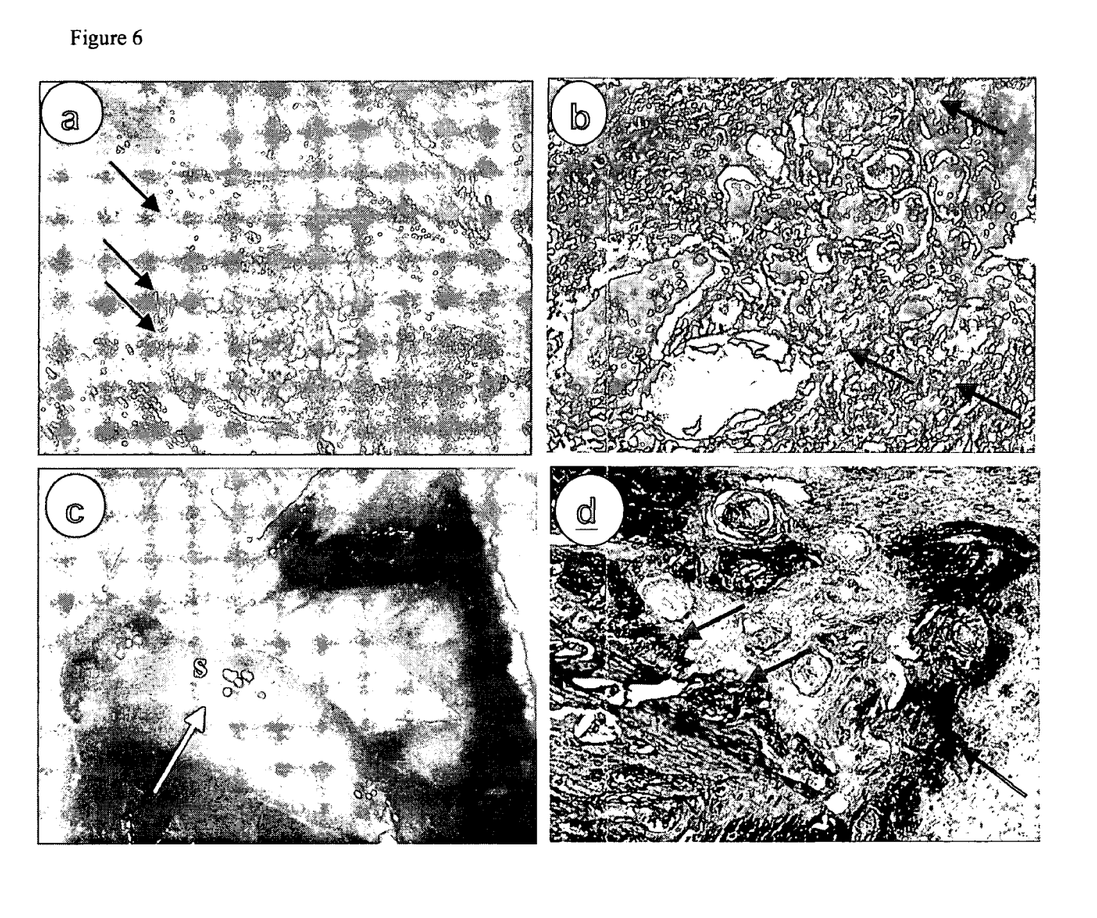
FIG. 6 shows in situ photomicroscopy of porous scaffold after 7 days CAM culture.

As can be seen in FIG. 6, the scaffold has remained aggregated, in situ, with extensive blood vessel invasion (arrows) from the CAM (magnification ×20). b) Paraffin section (5 um) of a) stained with alcian blue and sirius red demonstrating CAM ingrowth and matrix synthesis from CAM tissue (magnification ×50). c). In situ photomicroscopy of scaffold within chick femur defect after 7 days on CAM culture. Invasion of blood vessels (contrasted against blue paper) from CAM on and around the femur and scaffold (arrow, S) can be observed (magnification ×10). Scaffolds were generated using 25% biotin-PEG-biotin, 50% avidin saturated PLA-PEG-biotin microparticles and placed on femur defects. Explant-scaffold constructs were placed in CAM culture for 7 days. d) Paraffin section of scaffold within the femur wedge defect from c) stained for alkaline phosphatase activity. Alkaline phosphatase activity of CAM tissue and at the cut bone (B) edge integrated to the scaffold can be observed (magnification ×50).

The invention claimed is:

1. An open porous matrix of particulate material for in vivo use in or on a target tissue in medicine, the matrix comprising particles cross-linked with one another so as to define pores there between, each particle being cross-linked to one or more particles within the matrix, wherein the particles are formed from silk, elastin, chitin, chitosan, poly (α-hydroxyacids), poly(anhydrides), poly(orthoesters) or mixtures thereof.

2. A matrix according to claim 1, wherein the particles are between 1 nm and 1 mm.

3. A matrix according to claim 1, wherein the particles are between 100 nm and 500 μm.

4. A matrix according to claim 1, in which the poly (α-hydroxyacid) is selected from the group consisting of polyhydroxybutyric acid, lactic acid, polylactic acid, glycolic acid, polyglycolic acid, and s-caproic acid.

5. A matrix according to claim 1, in which the particle is hollow or absorbent.

6. A matrix according to claim 1, in which the matrix contains a substance to be released at or on a target site.

7. A matrix according to claim 6, in which some particles contain a bolus or boli of substance embedded with the particle for release at the target site.

8. A matrix according to claim 6, in which the substance is a drug, hormone, enzyme, nutrient, or other therapeutic agent, or mixtures thereof.

9. A matrix according to claim 6, in which the substance is selected from the group consisting of epidermal growth factor (EGF), nerve growth factor, insulin-like growth factor (IFG), basic fibroblast growth factor (bFGF), platelet derived growth factor (PDGF), transforming growth factor-P, cytokines, oestrogen, testosterone, kinases, chemokinases, sugars, amino acids, dopamine, amine-rich oligopeptides, amines, tamoxifen, cis-platin, and toxoids.

10. A matrix according to claim 1, in which the particles are biodegradable.

11. A matrix according to claim 1, in which the particles are biocompatible.

12. A matrix according to claim 1, in which the particles are cross-linked by a cross-linking agent which is a biologically active ligand.

13. A fluid composition comprising particulate material and a cross-linking agent whereby, in use, the particles cross-link to form a cross-linked matrix comprising particles cross-linked with one another so as to define pores there between on introduction to the cross-linking agent in or on a target tissue.

* * * * *